(12) United States Patent
Petrovic

(10) Patent No.: US 11,026,664 B1
(45) Date of Patent: Jun. 8, 2021

(54) ELECTROCHEMICAL DEVICE FOR VIRUS DETECTION AND TREATMENT

(71) Applicant: Slobodan Petrovic, Happy Valley, OR (US)

(72) Inventor: Slobodan Petrovic, Happy Valley, OR (US)

( * ) Notice: Subject to any disclaimer, the term of this patent is extended or adjusted under 35 U.S.C. 154(b) by 0 days.

(21) Appl. No.: 16/855,936

(22) Filed: Apr. 22, 2020

(51) Int. Cl.
*A61B 10/00* (2006.01)
*G01N 33/53* (2006.01)
*G01N 33/543* (2006.01)
*G01N 33/569* (2006.01)

(52) U.S. Cl.
CPC ..... *A61B 10/0051* (2013.01); *G01N 33/5306* (2013.01); *G01N 33/5438* (2013.01); *G01N 33/56983* (2013.01); *A61B 2560/0214* (2013.01); *A61B 2560/0468* (2013.01); *G01N 2333/165* (2013.01)

(58) Field of Classification Search
USPC .................................................. 600/300–301
See application file for complete search history.

(56) References Cited

U.S. PATENT DOCUMENTS

| | | | |
|---|---|---|---|
| 5,133,352 | A | 7/1992 | Lathrop et al. |
| 5,607,461 | A | 3/1997 | Lathrop |
| 6,594,527 | B2 | 7/2003 | Mo |
| 6,618,625 | B2 | 9/2003 | Silverstone |
| 2004/0167589 | A1 | 8/2004 | Heath |
| 2005/0125040 | A1 | 6/2005 | Lathrop |
| 2014/0197042 | A1* | 7/2014 | Zhang ................ G01N 27/3271 205/777.5 |
| 2015/0290454 | A1* | 10/2015 | Tyler ..................... G06F 3/0383 607/134 |

FOREIGN PATENT DOCUMENTS

| | | |
|---|---|---|
| EP | 1 359 971 | 3/2007 |
| WO | WO 01/78832 | 10/2001 |
| WO | WO 2010/062564 | 6/2010 |

OTHER PUBLICATIONS

Alar Ninla, et al, "Open-Source Potentiostat for Wireless Electrochemical Detection with Smartphones," Anal. Chem. 2018, 90, 6240-46, USA.
Diego Canton!, et al, "Ebolaviruses: New Rolse for old proteins," PLOS Negl Trop Dis 12(5): e0006349, https://doi.org/10.1371/journal.pntd.0006349 (May 3, 2018).
(Continued)

*Primary Examiner* — Nicole F Lavert
(74) *Attorney, Agent, or Firm* — Stephen J. Joncus

(57) ABSTRACT

Viruses, including corona viruses such as COVID-19, are often present in the mouth or nose of a person before they infect the body. The disclosed electrochemical device destroys or denatures viruses in the mouth or nose rendering the viruses ineffective to cause infection by applying a low voltage potential to the mucus. The device has a potentiostat powered by a small battery embedded in a plastic frame that fits in a person's mouth. The device has electrodes to contact the mucus of the mouth or nose. The mucus serves as electrolyte, conducting ions as well as viruses with their protein "skin" towards the electrode. The viruses are adsorbed onto the metal probes where the electrical current denatures the protein skin of the virus rendering the virus ineffective to cause infection.

10 Claims, 6 Drawing Sheets

(56) References Cited

OTHER PUBLICATIONS

Scott D. Adams, et al, "MiniStat: Development and Evaluation of a Mini-Potentiostat for Electrochemical Measurements," IEEE Access, 7, 31903-31912 (Mar. 4, 2019).
Jiajia Deng, et al, "Impedimetric DNA Biosensor Based on a Nanoporous Alumina Membrane for the Detection of the Specific Oligonucleiotide Sequence of Dengue Virus," Sensors 2013, 13, 7774-7785 (Jun. 17, 2013).
Lorenzo Russo, et al, "Low-Cost Strategy for the Development of a Rapid Electrochemical Assay for Bacteria Detection Based on AuAg Nanoshells," ACS Omega 2018, 3, 18849-18856 (Dec. 31, 2018).
Yeseren Saylan, et al, "An Alternative medical Diagnosis Method: Biosensors for Virus Detection," Biosensors 2019, 9, 65 (May 21, 2019).

\* cited by examiner

ELECTROCHEMICAL DEVICE FOR VIRUS DETECTION AND TREATMENT

BACKGROUND

Viruses, including corona viruses, enter a person's system through the mouth or nose and reside in the mucus of the mouth and nose. They stay in the mucus for an amount of time before they are able to invade the rest of the body. Infected persons with viruses in their mucus can spread it through coughing, sneezing, or speaking with others. There is a need for a device that can treat viruses in the mouth or nose before they have a chance to spread to the rest of the body or to others.

SUMMARY

Disclosed herein are electrochemical devices that treat, reduce, eliminate, test for, and measure viruses in the mucus of the mouth and nose. The device has a potentiostat powered by a small battery embedded in a plastic frame that fits in a person's mouth. The device has electrodes to contact the mucus of the mouth or nose. When the device is in place in the mouth, the metal probes of the electrodes contact the mucus while a insulating layer prevents the metal probes from coming in contact with the mucusa of the mouth or nose. When the device is in place, it creates an ionic current through the mucus that is undetectable by human senses. The mucus serves as electrolyte, conducting ions as well as viruses with their protein "skin" towards the electrodes. The viruses are adsorbed onto the metal probes where the electrical current denatures the protein skin of the virus rendering the virus ineffective to cause infection. The potential required to denature the protein skin of a virus is less than 1 volt. The actual voltage of the device can be adjusted and controlled to selectively treat a target virus. A person would apply this treatment several times in a day or for extended periods of time to destroy or disable any viruses present in the mucus. Additionally, a person could apply this treatment as a preventative to possible infection.

DESCRIPTION

Figure 1A:
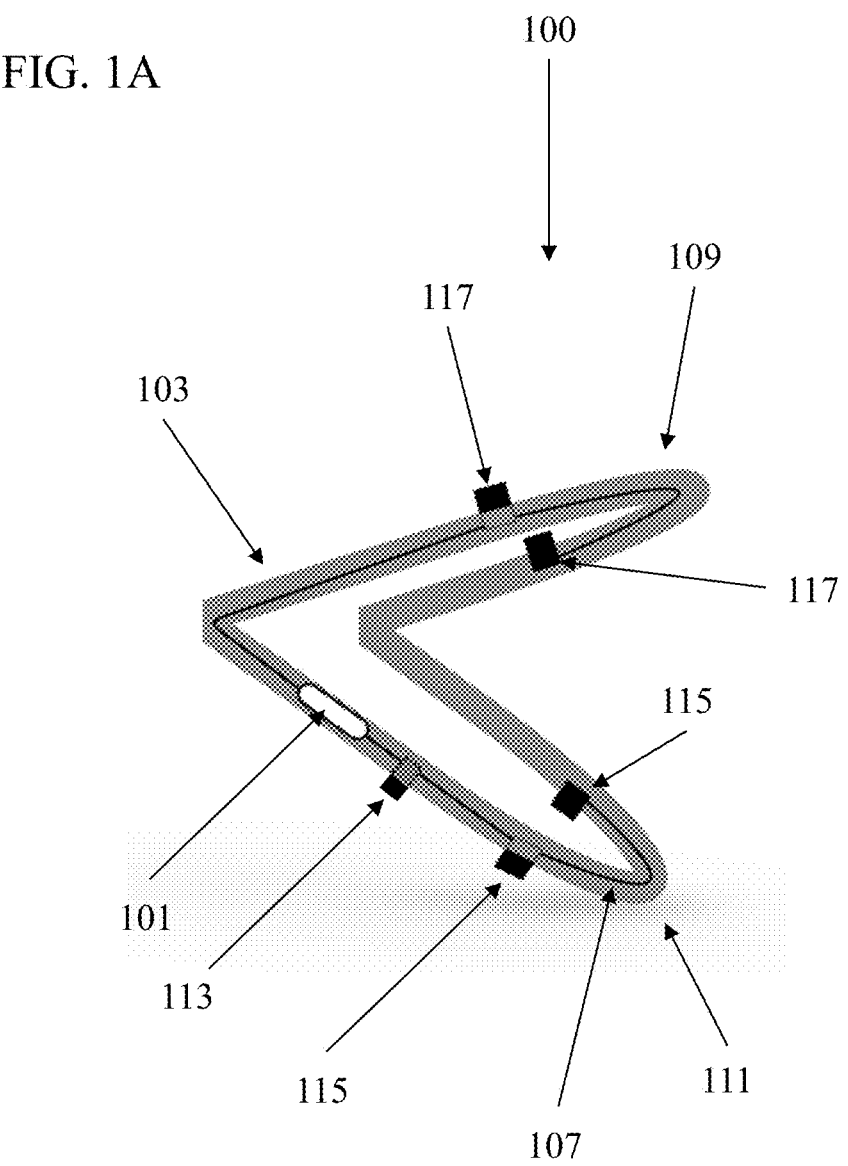
FIG. 1A is a schematic of one embodiment of an electrochemical device that treats, reduces, and eliminates viruses in the mucus of the mouth.
Figure 1B:
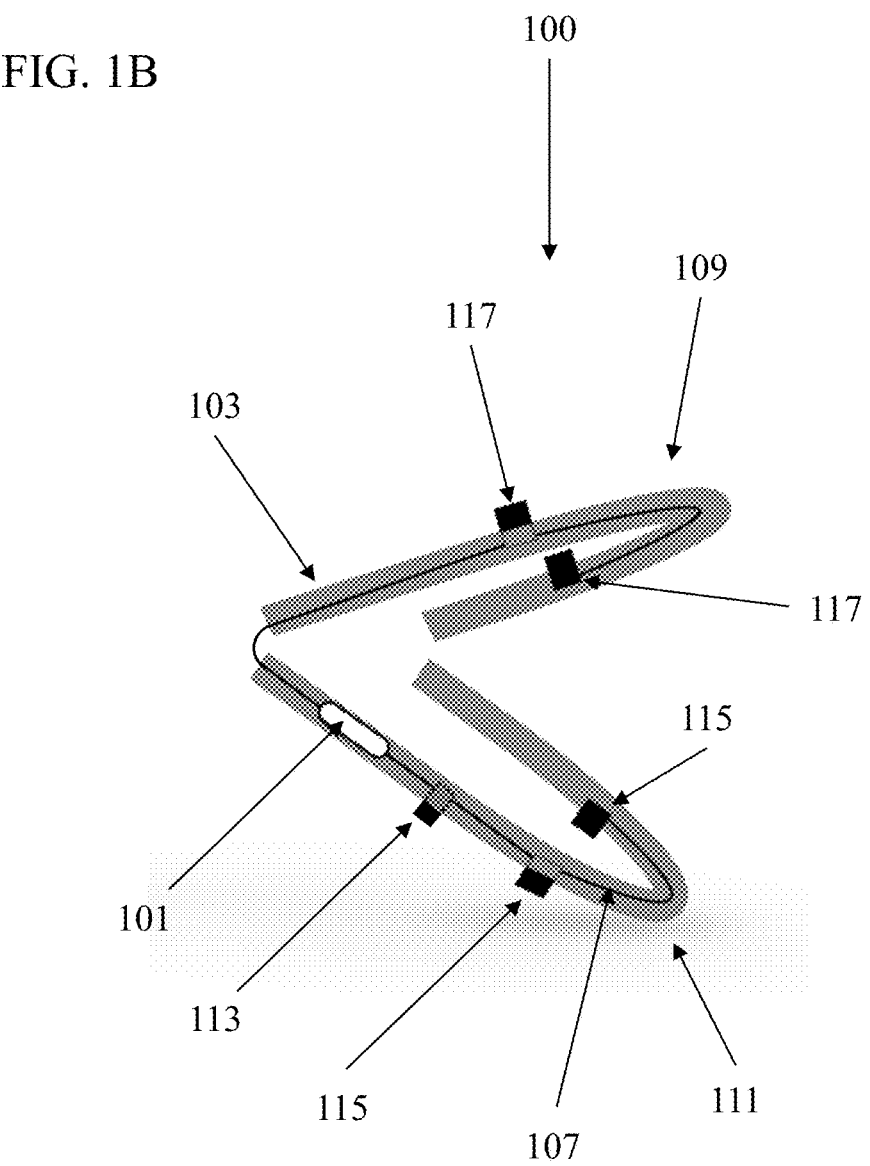
FIG. 1B is a schematic of another embodiment of an electrochemical device that treats, reduces, and eliminates viruses in the mucus of the mouth.
Figure 1C:
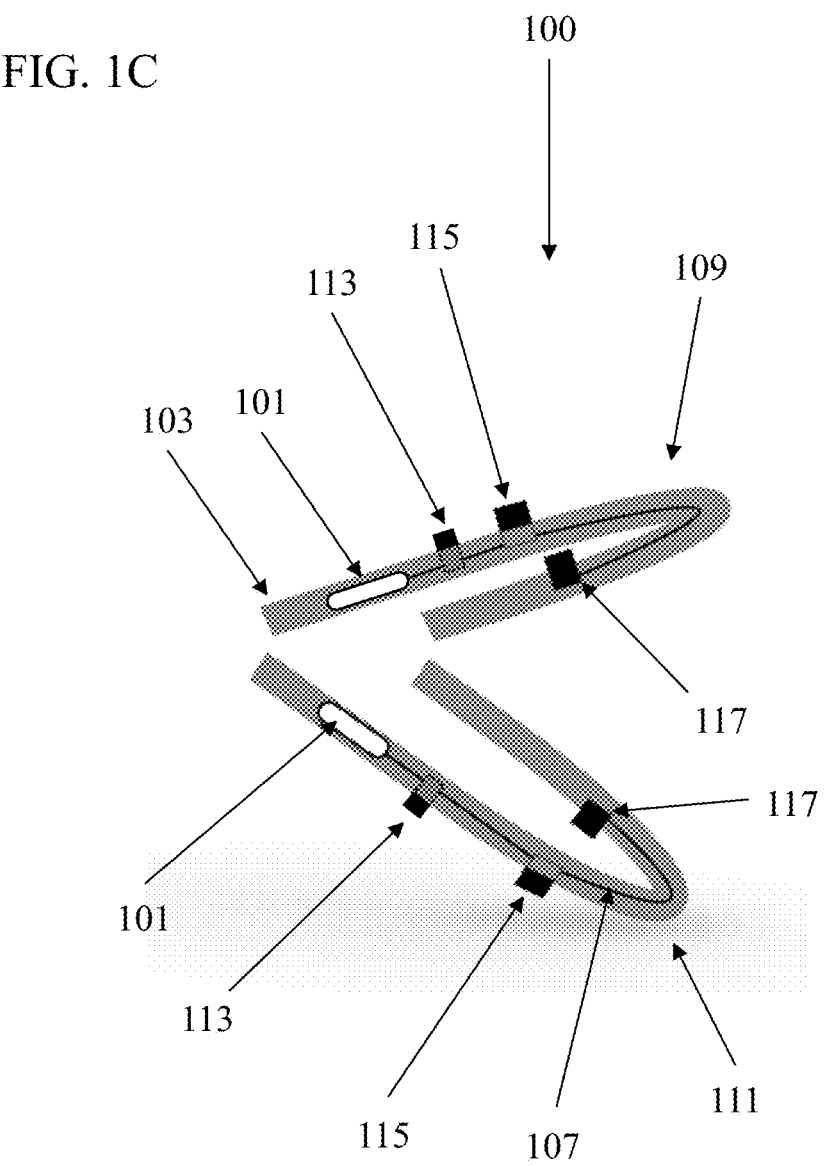
FIG. 1C is a schematic of another embodiment of an electrochemical device that treats, reduces, and eliminates viruses in the mucus of the mouth.

The electrochemical device for virus detection and treatment in the mouth 100 consists of a circuit powered by a battery assembly 101 with a mounting apparatus 103 that fits in the mouth, typically on the teeth, having an upper portion 109 to fit on the upper teeth and a lower portion 111 to fit on the lower teeth. The mounting apparatus 103 can be in any form that can fit over teeth to hold the elements of the circuit in place. It can be similar to an athletic mouth guard, or other device designed to fit in the mouth in a way that will hold the electrodes in place. FIG. 1A. shows a mounting apparatus 103 in which the upper 109 and lower 111 portions are hinged. A battery assembly 101 is connected by wires 107 embedded in the mounting apparatus 103 to one or more working electrodes 115 in the lower portion 111, one reference electrode 113 in the lower portion 111, and one or more counter electrodes 117 in the upper portion 109. A basic configuration is one working electrode 115 and one counter electrode 117. Additional working or counter electrodes are wired in series with the first working or counter electrode respectively. Mounting apparatus 103, as depicted in FIGS. 1A, 1B, and 1C, would cover all or most of the teeth, but many possible configurations are possible to hold the battery assembly 101, wire 107, and electrodes in the mouth. The reference electrode 113 is preferred, but not required.

FIG. 1B shows an alternate embodiment of the electrochemical device 100 where the upper 109 and lower 111 portions of the mounting apparatus are not hinged, but are connected by a wire 107 that connects the counter electrodes 117 in the upper portion 109 with the battery assembly 101, the reference electrode 113, and working electrodes 115 in the lower portion.

FIG. 1C shows an alternative embodiment of the electrochemical device 100 where the upper portion 109 and the lower portion 111 are electrically and mechanically independent of each other. Each the upper 109 and lower 111 portions have their own battery allowing them to be used together or separately. The battery in the upper portion 109 is connected to a working electrode 115, reference electrode 113, and counter electrode 117. Likewise, the battery assembly 101 in the lower portion 111 is connected to a working electrode 115, reference electrode 113, and counter electrode 117.

The mounting apparatus 103 can be made of any plastic material that can be molded into a an appropriate shape to fit over teeth while having the battery 101 embedded and the electrodes exposed. The material for the mounting apparatus 103 can be variety of plastics such as EVA (Ethylene vinyl acetate), PTFE (polytetrafluoroethylene), PVDF (polyvinylidene difluoride), or PVC (polyvinyl chloride). The mounting apparatus 103 can be formed to mount on all or some of a person's teeth, or in another fashion in the mouth, not necessarily over the teeth, to hold the electrodes in place. The electrodes (working electrode 115, reference electrode 113, and counter electrode 117) may be located inside the teeth and gums or outside the teeth and gums.

The battery assembly 101 is preferably as potentiostat powered by a small battery. The type of battery in the battery assembly 101 can be, but no limited to, a primary (ZnO, Leclanche, or alkaline) battery, with the option to easily replace the battery. Alternatively, a rechargeable battery can be used, such as nickel metal hydride or lithium polymer, along with an appropriate mechanism for recharging the battery.

Figure 2:
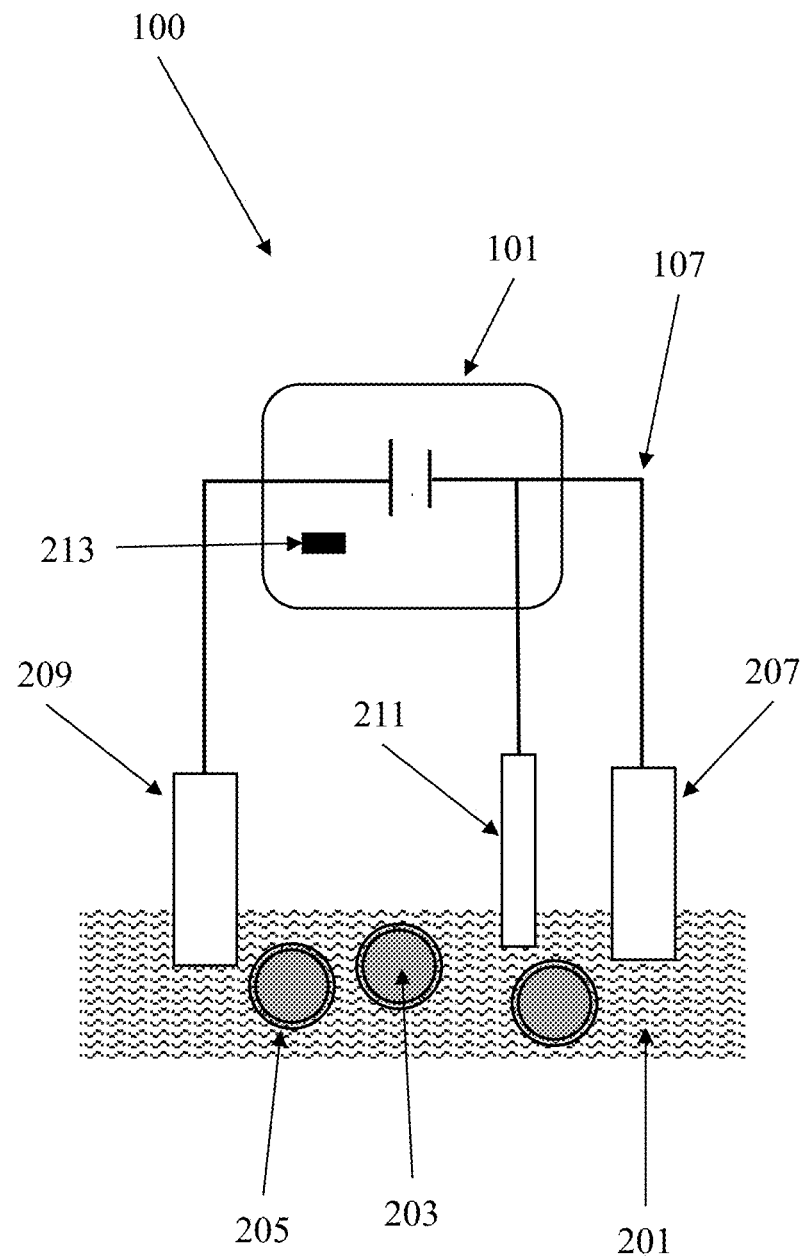
FIG. 2 is a schematic of the electrical connections between the electrochemical device and mucus with viruses present.

The potentiostat in the battery assembly 101 preferably has a working electrode 207, a counter electrode 209, and a reference electrode 211 which are then in contact with mucus 201 in the mouth or nose as shown in FIG. 2. A reference electrode 211 permits a potentiostat to more accurately control the voltage. Alternatively, the potentiostat may omit the reference electrode resulting in less precise control of voltage, but still sufficient to effectively destroy viruses. As a result of the voltage applied by the potentiostat of the battery assembly 101, a small ionic current is created in the mucus 201 between the working electrode 207 and the counter electrode 209.

Viruses 203, including corona viruses, have a protein skin 205 that can be destroyed or denaturated with small electric currents and low potential. The small electric currents and low potential in the potentiostat creates an ionic current in the mucus 201. The ionic current drives the viruses 203 in the mouth towards the working electrode 207 where they adhere. When a virus 203 becomes adhered to the working electrode 207, the protein skin 205 of the virus 203 is destroyed or denaturated by the current from the battery assembly 101, rendering the virus 203 incapable of causing infection. An electric potential of less than 1 volt is sufficient to create a current that will denaturate the protein skin 205 of a virus 203, including the nucleocapsid protein and the spike protein found in the COVID-19 virus.

Preferably, the voltage of the potentiostat of the battery assembly 101, can be adjusted. Adjustment of the voltage may be useful in targeting particular viruses of concern that are, or may be, in the mucus 201. The potentiostat may configured with a manual dial mounted flush to the electrochemical device 100 or remotely using a wireless transceiver such as a Bluetooth transceiver 213 to connect with a smart phone or other computing device with an application designed to interface with the electrochemical device 100.

Figure 3:
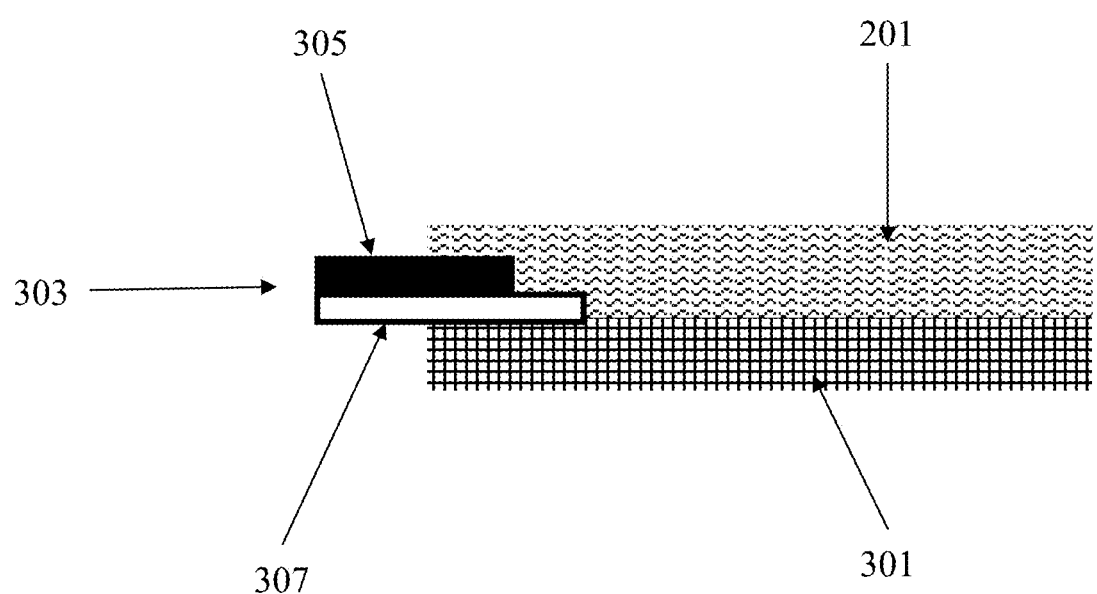
FIG. 3 depicts a configuration for a electrode.

As shown in FIG. 3 the electrodes 303 (consisting of the working electrode 207, counter electrode 209, and the reference electrode 211) are designed to contact the mucus 201 but not the mucosa (the moist tissue of the mouth or nose) 301 to prevent the electric potential applied by the electrochemical device 100 from being detected by human senses. The electrode 303 consists of an insulating layer 307 that comes in direct contact with the mucosa 301 and a metal probe 305 that only comes in with the mucus 201. The electrodes 303 may be shaped with an increased surface area that will lightly adhere to the gum tissue.

The electrochemical device 100 does not apply the voltage potential to the mucosa 301. Rather, the electrochemical device 100 applies the voltage potential to the mucus 201 establishing an electrochemical cell to treat the virus 203. This electrochemical cell encompasses the entire interior surface of the mouth covered with mucus/electrolyte 201. The pH of mucus 201 is typically close to neutral; however, it contains sufficient electrolytes for ion conductivity and protein transport. The conductivity of the mucus 201 can also be enhanced by drinking or gargling a slightly acidic solution including a cola soft drink or similar that would lower the pH of the mucus temporarily and enable a higher ionic current and faster transport of the viruses to the working electrode 207 where they will be destroyed.

The ionic current distribution through the mucus 201 in the mouth varies depending on the distance from the electrodes 303, and other anatomic features of the mouth. However, prolonged use will gradually provide a sufficient driving force for the viruses to move from every part of the mouth towards the working electrode 207. The movement of virus proteins towards the working electrode 207 is driven by the cell voltage, diffusion, and the concentration gradient.

The voltage necessary to adsorb protein on the surface of the metal probe 305 is low, on the order of 0.2 to 0.4 V, but higher voltages up to 1 V may be used to overcome a potentially high ionic resistance in the mucus 201. The voltage can be tuned for a particular pathogen to values known to be effective for adsorption and charge transfer. The electrochemical device 100 can be used to detect the presence of virus. Using a technique called chronoamperometry, the electrochemical device 100 can be configured and used for detection of the concentration of a particular virus. When connected wirelessly to a smart phone or other computing device, chronoamperometry data measured by the electrochemical device 100 can be analyzed and/or transmitted through the Internet to medical services for analysis.

The metal probes 305 can be made a number of metals such as gold, palladium, copper, or silver. The metal probes 305 may be modified using special compounds containing receptors for particular proteins designed to enable more readily electron transfer to protein. The dimensions of the metal probes 305 can typically be from 0.1 to 20 mm in length and 20 microns to 5 millimeters in width. It is also possible for the metal probes 305 to be formed in an array, so called micro-electrodes, for added sensitivity. The metal probes 305 can also be modified to embed small rotating electrodes using small electric motors. Rotation of the electrodes provides for better mass transport of mucus to the electrodes.

Figure 4:
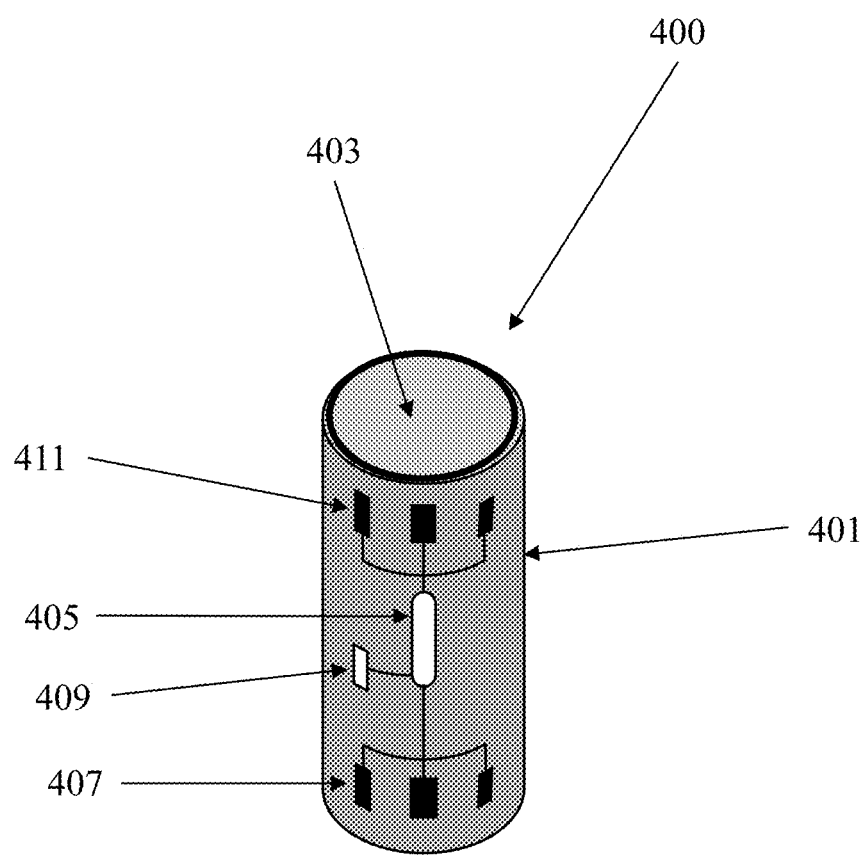
FIG. 4 shows an embodiment of an electrochemical device that treats, reduces, and eliminates viruses in the mucus of the nose.

The electrochemical device for virus detection and treatment in the nose 400 can also be configured to fit in a nostril of the nose as shown in FIG. 4. The mounting apparatus 401 is cylindrically shaped tube shaped to fit in a nostril with an orifice 403 and permit breathing. The mounting apparatus 401 may be made of various soft plastic materials to make its presence in the a nostril as comfortable as possible. The electrochemical device 400 has a battery assembly with one or more working electrodes 407, a reference electrode 409, and one or more counter electrodes 411. Because there is much less mucus 201 in the nose than in the mouth, the electrochemical device 400 may be coated with a gel before inserting that will facilitate ionic transfer of viruses in the nose to the working electrode. When the gel is in contact with mucus it will create a sufficient layer of electrolyte to enable the electrochemical reaction. The features and options for a electrochemical device 400 designed to be inserted in a nostril are the same as described for a electrochemical device 100 configured to be inserted in the mouth.

What is claimed is:

1. An apparatus comprising:
   a mount configured to fit in the mouth or nose of a person;
   a potentiostat having two electrodes, a working electrode and a counter electrode;
   a battery;
   said working electrode having a first insulating layer; and
   said counter electrode having a second insulating layer.

2. The apparatus of claim 1 further comprising:
   a reference electrode;
   said reference electrode having a third insulating layer.

3. The apparatus of claim 1 further comprising:
   a wireless transceiver; and
   said potentiostat having a voltage that is adjustable via the wireless transceiver.

4. The apparatus of claim 1 further comprising:
   said potentiostat having adjustable voltage; and
   a manual dial for adjusting voltage.

5. An apparatus comprising:
   a mounting apparatus having a battery, a working electrode, and a counter electrode;
   said mounting apparatus configured to be inserted in a person's mouth having mucosa and mucus;
   said working electrode having a first metal probe and a first insulator wherein the first insulator is positioned between the mucosa and the first metal probe;
   said counter electrode having a second metal probe and a second insulator wherein the second insulator is positioned between the mucosa and the second metal probe.

6. The apparatus of claim 5 further comprising:
a potentiostat.
7. The apparatus of claim 6 further comprising:
a reference electrode.
8. The apparatus of claim 6 further comprising:
said potentiostat having adjustable voltage; and
a manual actuator for adjusting voltage.
9. The apparatus of claim 6 further comprising:
said potentiostat having adjustable voltage and a wireless transceiver.
10. An apparatus comprising:
a means for holding a first metal probe in contact with mucus in the mouth without the first metal probe coming in contact with mucusa in the mouth;
a means for holding a second metal probe in contact with mucus in the mouth without the second metal probe coming in contact with mucusa in the mouth;
a means for holding a reference metal probe in contact with mucus in the mouth without the reference metal probe coming in contact with mucosa in the mouth;
a battery;
a potentiostat having a voltage; and
a means to adjust the voltage of said potentiostat.

\* \* \* \* \*